(12) United States Patent
Truppo et al.

(10) Patent No.: US 7,238,503 B2
(45) Date of Patent: Jul. 3, 2007

(54) PROCESS FOR MAKING FLUOROLEUCINE ETHYL ESTERS

(75) Inventors: Matthew D. Truppo, Tinton Falls, NJ (US); Jeffrey C. Moore, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/514,738

(22) Filed: Aug. 31, 2006

(65) Prior Publication Data

US 2007/0059812 A1    Mar. 15, 2007

(51) Int. Cl.
*C12P 13/06* (2006.01)
*C12P 13/04* (2006.01)
*C12N 9/18* (2006.01)
*C12N 9/20* (2006.01)
*C07C 229/00* (2006.01)

(52) U.S. Cl. ................ 435/116; 435/106; 435/129; 435/197; 435/198; 514/561; 562/553

(58) Field of Classification Search .............. 435/116, 435/106, 129, 197, 198; 514/561; 562/553
See application file for complete search history.

(56) References Cited

U.S. PATENT DOCUMENTS

2005/0234128 A1\* 10/2005 Devine et al. ............. 514/561

\* cited by examiner

*Primary Examiner*—Herbert J. Lilling
(74) *Attorney, Agent, or Firm*—Nicole M. Beeler; David A. Muthard

(57) ABSTRACT

The instant invention describes a novel reaction that includes spontaneous racemization of an azalactone via enol tautomerization. This racemization results in improved yield and ee over other reactions previously described.

6 Claims, No Drawings

PROCESS FOR MAKING FLUOROLEUCINE ETHYL ESTERS

BACKGROUND OF THE INVENTION

The asymmetric synthesis of γ-fluoroleucine-α-amino acids is a proven technology for the production of potential pharmaceutical compounds that have a wide array of biological uses, including enzyme inhibitors, receptor antagonists and lipophilicity enhancing agents. The use of enzyme mediated dynamic kinetic resolution ring opening of azalactones has been demonstrated as an effective way of introducing stereochemistry in γ-fluoroleucine ethyl ester compounds.

The instant invention describes a novel reaction that includes spontaneous racemization of an azalactone via enol tautomerization. This racemization results in improved yield and ee over other reactions previously described. Additionally, the instant invention is suitable for large scale production. Previously known processes were not economically feasible for large scale production, specifically because of the large amount of enzyme required to run the reactions The fed batch reactor makes the enzymatic production of fluoroleucine ethyl ester economically feasible for large scale production. An increased temperature over previously known processes, along with a substrate charging strategy, reduces the enzyme to substrate ratio to 1:4. The ester yield is also increased about 5% over previously known processes.

The plug flow column reactor solves the problem of enzyme deactivation by extending enzyme life about 20 fold versus previously known processes. Enzyme deactivation, due to shear in batch systems, is reduced from about 10% per hour to 0.5% per hour. The column process uses a 1:20 ratio of enzyme to substrate and provides for ester product with 90% yield and 86% ee, which is a greater than 20 fold improvement over previously known processes. Also, the column process shows a large cost reduction in the amount of enzyme that is needed.

SUMMARY OF THE INVENTION

By this invention, there is provided a process for preparing a compound of formula I:

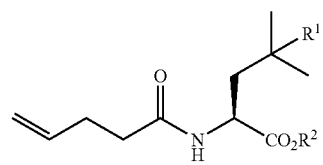

wherein $R^1$ is halo and $R^2$ is $C_{1-4}$ alkyl;

comprising an enzyme mediated ring opening of an azalactone of formula II:

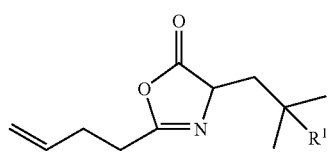

DETAILED DESCRIPTION OF THE INVENTION

By this invention, there is provided a process for the preparation for a compound of formula I:

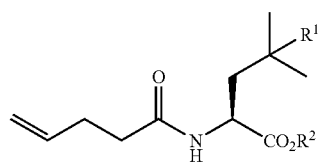

wherein $R^1$ is halo and $R^2$ is $C_{1-4}$ alkyl;

comprising an enzyme mediated ring opening of an azalactone of formula II:

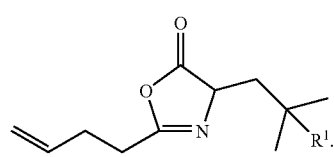

In a class of the invention, $R^1$ is fluoro and $R^2$ is ethyl.

The enzyme mediated ring opening is performed with a hydrolytic enzyme selected from *Candida antarctica* lipase B, *Pseudomonas fluorescens* lipase, *Pseudomonas cepacia* lipase, cholesterol esterase, Porcine pancreas lipase, pancreatin, *Candida antarctica* lipase A, *T. linaginosa* (Lipase), Porcine liver lipase, *P. stutzeri* lipase and *Mucor miehei* lipase. In a class of the invention, the enzyme is *Candida antarctica* lipase B.

In one embodiment of the invention, the process is run as a fed batch reaction. The fed batch reaction is carried out in a temperature controlled stirred tank reactor where agitation is carried out with overhead stirring via a pitched blade impeller. This agitation needs to be sufficient to suspend the immobilized enzyme resin. In a class of the invention, the fed batch reaction is carried out at a temperature of about 50° to about 65° C. In a subclass of the invention, the fed batch reaction is carried out at a temperature of about 65° C. The fed batch reaction can be carried out in an organic solvent such as MTBE THF, DMF, toluene, $CH_3CN$ and mixtures thereof. In a class of the invention, the fed batch reaction is carried out in MTBE.

With the fed batch reaction, it is preferable to always maintain a high enzyme to substrate ratio and to feed the substrate over time, as opposed to a higher starting concentration of substrate, to minimize background ethanolysis and hydrolysis.

In another embodiment of the invention, the process is a continuous plug flow column reaction. The immobilized enzyme is slurried in MTBE and then packed into the column under atmospheric pressure. Two feed solutions are made, the first solution comprising an azalactone of formula II and a second solution comprising amine base and EtOH. In a class of the invention, the amine base is triethylamine, DBU, 2,6-lutidine or DABCO. In a subclass of the invention, the amine base is triethylamine.

With the column reaction, it is preferable to keep the two feeds (i.e., the azlactone feed and the Et3N/EtOH feed) separate before entering the column to minimize background ethanolysis. Background ethanolysis can result when the azalactone comes in contact with the EtOH. An advantage of the column reaction system is the elimination of enzyme degradation or deactivation due to shear from mixing in batch systems, which decreases enzyme deactivation rate by >20 fold.

Important to both the fed batch and column reactions is running them at high (~65° C.) temperatures to increase enzymatic rate relative to background rates of ethanolysis and hydrolysis. Running the reactions at high temperature boosts yield and ee.

The term "alkyl" shall mean a substituting univalent group derived by conceptual removal of one hydrogen atom from a straight or branched-chain acyclic saturated hydrocarbon (i.e., —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, etc).

The term "halo" shall include iodo, bromo, chloro and fluoro.

An illustration of the processes of the present invention is described by the following general scheme, using appropriate materials. The specific examples following the scheme further exemplify the processes of the present invention. The compounds illustrated in the scheme and examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

SCHEME

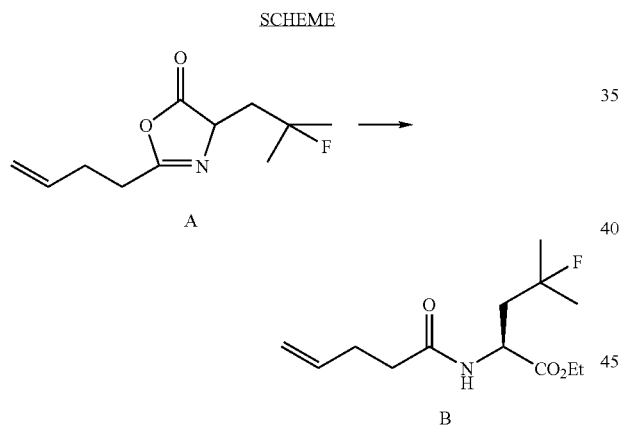

EXAMPLE 1

Fed Batch Process

Azlactone substrate A is dissolved in MTBE. EtOH and $Et_3N$ are then added to the azlacetone in MTBE solution. Immobilized enzyme from *Candida antarctica* lipase B is then added so that the final concentrations in the resulting solution are 80 g/L azlactone A, 86 g/L EtOH, 7.6 g/L $Et_3N$, and 80 g/L immobilized enzyme. The solution is heated to 50° C. and mixed with agitation sufficient to suspend the immobilized enzyme. The reaction is aged for 0.5 hours and an addition of azlactone A and EtOH is added (i.e. 80 g azlactone and 17.2 g of EtOH for a 1 L reaction). The reaction is then aged for 1 hour and an addition of azlactone A and EtOH is added (i.e. 80 g azlactone and 17.2 g of EtOH for a 1 L reaction). The reaction is aged for 1.5 hours and an addition of azlactone A and EtOH is added (i.e. 80 g azlactone and 17.2 g of EtOH for a 1 L reaction). The reaction is aged for 3 hours and assayed for completion and the formation of product B.

EXAMPLE 2

Continuous Plug Flow Column Process 50 g of immobilized enzyme from *Candida antarctica* lipase B is slurried in MTBE and packed in a jacketed column under atmospheric pressure. 1 kg of azlactone A is dissolved in MTBE so that 6.25 L of a solution containing 160 g/L azlactone A in MTBE is made. 6.25 L of a second solution of 172 g/L EtOH and 15.2 g/L $Et_3N$ in MTBE is made. The column jacket is set to 65° C. and the two solutions are fed at equal rates and mixed just before entering the top of the column. The two solutions can be fed via pumps or pressurized holding tanks and the total volume is fed over 20 hours. The outlet at the bottom of the column is fed through a back pressure regulator set at 20 psi to prevent the solution from boiling. After going through the back pressure regulator, the solution is fed to a quench tank containing 1N $H_2SO_4$. The quench tank is then assayed for product B.

What is claimed is:

1. A process for preparing a compound of formula I:

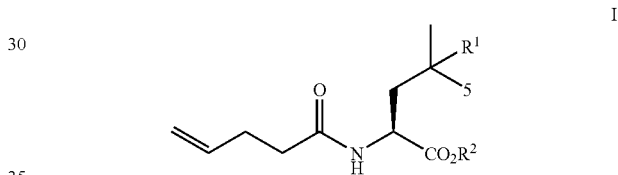

wherein $R^1$ is halo and $R^2$ is $C_{1-4}$ alkyl;
comprising an enzyme mediated ring opening of an azalactone of formula II: which process is a continuous plug flow column reaction

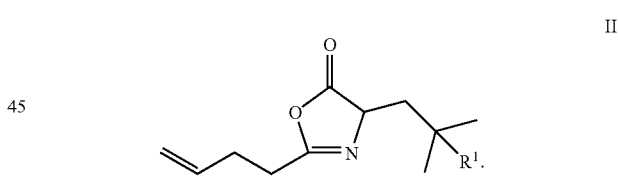

2. The process of claim 1 wherein wherein $R^1$ is fluoro and $R^2$ is ethyl.

3. The process of claim 2 wherein the enzyme is *Candida antarctica* lipase B, *Pseudomonas fluorescens* lipase, *Pseudomonas cepacia* lipase, cholesterol esterase, Porcine pancreas lipase, pancreatin, *Candida antarctica* lipase A, *T. lanuginosa*, Porcine liver lipase, *P. stutzeri* lipase, *Mucor miehei* lipase.

4. The process of claim 3 wherein the enzyme is *Candida antarctica* lipase B.

5. The process of claim 1 wherein the continuous plug flow column is fed with a first solution comprising an azalactone of formula II and a second solution comprising and amine base and EtOH.

6. The process of claim 5 wherein the amine base is triethylamine.

* * * * *